(12) United States Patent
Stadler et al.

(10) Patent No.: US 9,199,087 B2
(45) Date of Patent: Dec. 1, 2015

(54) APPARATUS AND METHOD FOR SELECTING A PREFERRED PACING VECTOR IN A CARDIAC RESYNCHRONIZATION DEVICE

(75) Inventors: Robert W. Stadler, Shoreview, MN (US); Aleksandre T. Sambelashvili, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 735 days.

(21) Appl. No.: 13/301,043

(22) Filed: Nov. 21, 2011

(65) Prior Publication Data

US 2013/0131751 A1    May 23, 2013

(51) Int. Cl.
*A61N 1/368*    (2006.01)

(52) U.S. Cl.
CPC ............ *A61N 1/3684* (2013.01); *A61N 1/3686* (2013.01)

(58) Field of Classification Search
None
See application file for complete search history.

(56) References Cited

U.S. PATENT DOCUMENTS

| | | |
|---|---|---|
| 5,117,824 A | 6/1992 | Keimel |
| 5,458,624 A | 10/1995 | Renirie et al. |
| 5,658,318 A | 8/1997 | Stroetmann et al. |
| 5,683,432 A | 11/1997 | Goedeke et al. |
| 5,707,398 A | 1/1998 | Lu |
| 5,814,076 A | 9/1998 | Brownlee |
| 5,814,088 A | 9/1998 | Paul et al. |
| 5,873,898 A | 2/1999 | Hemming |
| 5,897,577 A | 4/1999 | Cinbis et al. |
| 5,913,308 A | 6/1999 | Forbes et al. |
| 6,016,448 A | 1/2000 | Busacker et al. |
| 6,128,535 A | 10/2000 | Maarse |
| 6,185,460 B1 | 2/2001 | Thompson |
| 6,317,633 B1 | 11/2001 | Jorgenson et al. |
| 6,332,096 B1 | 12/2001 | Mower |
| 6,393,316 B1 | 5/2002 | Gillberg |
| 6,418,346 B1 | 7/2002 | Nelson et al. |
| 6,442,433 B1 | 8/2002 | Linberg |
| 6,477,417 B1 | 11/2002 | Levine |
| 6,480,745 B2 | 11/2002 | Nelson |
| 6,599,250 B2 | 7/2003 | Webb |
| 6,611,712 B2 | 8/2003 | Spinelli |
| 6,622,045 B2 | 9/2003 | Snell |
| 6,687,545 B1 | 2/2004 | Lu |
| 6,704,598 B2 | 3/2004 | Ding |
| 6,772,008 B2 | 8/2004 | Zhu et al. |
| 6,820,019 B1 | 11/2004 | Kelly et al. |
| 6,901,293 B2 | 5/2005 | Rogers et al. |
| 6,950,701 B2 | 9/2005 | Begemann |

(Continued)

OTHER PUBLICATIONS

Bogaard M., et al., Difference between paced interventricular conduction times can be neglected in automatic algorithm optimization of the interventricular delay for cardiac resynchronization therapy, Heart Rhythm 2010, vol. 7, No. 5 (Suppl), p. S304.

(Continued)

*Primary Examiner* — Erica Lee
(74) *Attorney, Agent, or Firm* — Michael C. Soldner

(57) ABSTRACT

A medical device and associated method control the delivery of a cardiac pacing therapy including selecting left ventricular pacing sites for delivering the therapy. The left ventricular pacing sites are selected by delivering pacing pulses to a patient's left ventricle at multiple pacing sites one at a time and determining right ventricular activation times in response to the pacing pulses being delivered at each of the pacing sites. A left ventricular pacing site is selected in response to the determined right ventricular activation times.

9 Claims, 5 Drawing Sheets

(56) References Cited

U.S. PATENT DOCUMENTS

| | | |
|---|---|---|
| 7,107,093 B2 | 9/2006 | Burnes |
| 7,123,963 B2 | 10/2006 | Sawchuk |
| 7,123,964 B2 | 10/2006 | Betzold et al. |
| 7,142,923 B2 | 11/2006 | North et al. |
| 7,181,284 B2 | 2/2007 | Burnes et al. |
| 7,239,913 B2 | 7/2007 | Ding |
| 7,254,442 B2 | 8/2007 | Van Gelder et al. |
| 7,292,889 B2 | 11/2007 | Gordon |
| 7,324,949 B2 | 1/2008 | Bristol |
| 7,340,302 B1 | 3/2008 | Falkenberg et al. |
| 7,392,086 B2 | 6/2008 | Sathaye |
| 7,555,336 B2 | 6/2009 | Sheth |
| 7,680,536 B2 | 3/2010 | Sathaye et al. |
| 7,697,977 B2 | 4/2010 | Yonce |
| 7,697,985 B2 | 4/2010 | Kaiser et al. |
| 7,706,879 B2 | 4/2010 | Burnes et al. |
| 7,751,882 B1 | 7/2010 | Helland |
| 7,787,948 B2 | 8/2010 | Ross et al. |
| 7,787,951 B1 | 8/2010 | Min |
| 7,848,807 B2 | 12/2010 | Wang |
| 7,848,812 B2 | 12/2010 | Crowley et al. |
| 7,894,894 B2 | 2/2011 | Stadler et al. |
| 8,165,297 B2 | 4/2012 | Hoffmann |
| 8,209,013 B2 | 6/2012 | Brooke et al. |
| 8,401,639 B2 | 3/2013 | McCabe et al. |
| 8,401,646 B2 | 3/2013 | Stadler et al. |
| 8,527,050 B2 | 9/2013 | Stadler et al. |
| 8,626,291 B2 | 1/2014 | Stadler et al. |
| 8,639,333 B2 | 1/2014 | Stadler et al. |
| 8,682,433 B2 | 3/2014 | Sheldon et al. |
| 8,954,160 B2 | 2/2015 | Splett et al. |
| 2002/0161328 A1 | 10/2002 | Rogers |
| 2002/0177879 A1 | 11/2002 | Ding et al. |
| 2003/0083709 A1 | 5/2003 | Zhu et al. |
| 2004/0098056 A1 | 5/2004 | Ding et al. |
| 2004/0102812 A1 | 5/2004 | Yonce et al. |
| 2004/0172079 A1 | 9/2004 | Chinchoy |
| 2005/0149138 A1* | 7/2005 | Min et al. ............... 607/27 |
| 2008/0071318 A1 | 3/2008 | Brooke et al. |
| 2008/0077186 A1 | 3/2008 | Thompson et al. |
| 2008/0077189 A1 | 3/2008 | Ostroff |
| 2008/0177344 A1 | 7/2008 | Maskara |
| 2008/0288015 A1 | 11/2008 | Tehrani et al. |
| 2008/0294218 A1 | 11/2008 | Savage et al. |
| 2009/0030470 A1 | 1/2009 | Holmstrom |
| 2009/0043351 A1 | 2/2009 | Sathaye et al. |
| 2009/0043352 A1 | 2/2009 | Brooke |
| 2009/0054942 A1 | 2/2009 | Zhu et al. |
| 2009/0054946 A1 | 2/2009 | Sommer et al. |
| 2009/0156957 A1 | 6/2009 | Linder et al. |
| 2009/0210024 A1 | 8/2009 | M. |
| 2009/0240298 A1 | 9/2009 | Lian |
| 2010/0042174 A1 | 2/2010 | Koh et al. |
| 2010/0100148 A1* | 4/2010 | Min et al. ............... 607/27 |
| 2010/0114211 A1 | 5/2010 | Donofrio et al. |
| 2010/0121396 A1 | 5/2010 | Gill et al. |
| 2010/0121404 A1 | 5/2010 | Bjorling |
| 2010/0137935 A1 | 6/2010 | Parikh |
| 2010/0137993 A1 | 6/2010 | Parrott et al. |
| 2010/0262204 A1 | 10/2010 | McCabe |
| 2010/0268059 A1 | 10/2010 | Ryu |
| 2010/0305637 A1 | 12/2010 | McCabe et al. |
| 2010/0305638 A1 | 12/2010 | McCabe et al. |
| 2010/0331906 A1 | 12/2010 | Williamson |
| 2011/0004264 A1 | 1/2011 | Siejko et al. |
| 2011/0022110 A1 | 1/2011 | Min |
| 2011/0022111 A1 | 1/2011 | Min |
| 2011/0022112 A1 | 1/2011 | Min |
| 2011/0098770 A1 | 4/2011 | Ryu et al. |
| 2011/0098772 A1 | 4/2011 | Min |
| 2011/0137369 A1 | 6/2011 | Ryu et al. |
| 2011/0178567 A1 | 7/2011 | Pei |
| 2012/0101546 A1* | 4/2012 | Stadler et al. ............ 607/28 |
| 2014/0074177 A1 | 3/2014 | Sathaye et al. |

OTHER PUBLICATIONS

Robert W. Stadler, et al., Method for Efficient Delivery of Dual Site Pacing, U.S. Appl. No. 13/301,084, P0040762.USU1, filed Nov. 21, 2011.

P0040762WOU2 (PCT/US2012/064031) PCT Notification of Transmittal of the International Search Report and the Written Opinion of the International Search Authority.

* cited by examiner

APPARATUS AND METHOD FOR SELECTING A PREFERRED PACING VECTOR IN A CARDIAC RESYNCHRONIZATION DEVICE

FIELD OF THE DISCLOSURE

The disclosure relates generally to medical devices and, in particular, to a medical device and associated method for controlling cardiac resynchronization therapy.

BACKGROUND

Cardiac resynchronization therapy (CRT) is a treatment for heart failure patients in which one or more heart chambers are electrically stimulated (paced) to restore or improve heart chamber synchrony. Among other factors, achieving a positive clinical benefit from CRT is dependent on the location of the pacing site, particularly in the left ventricle (LV). Thus, placement of the pacing leads, especially an LV pacing lead is important in promoting a positive outcome from CRT. As multipolar cardiac pacing leads become commercially available, multiple pacing electrode vectors are possible, for example, for pacing in the LV. A need remains for selecting which pacing electrode vector(s) are used for delivering CRT in a most efficacious way.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
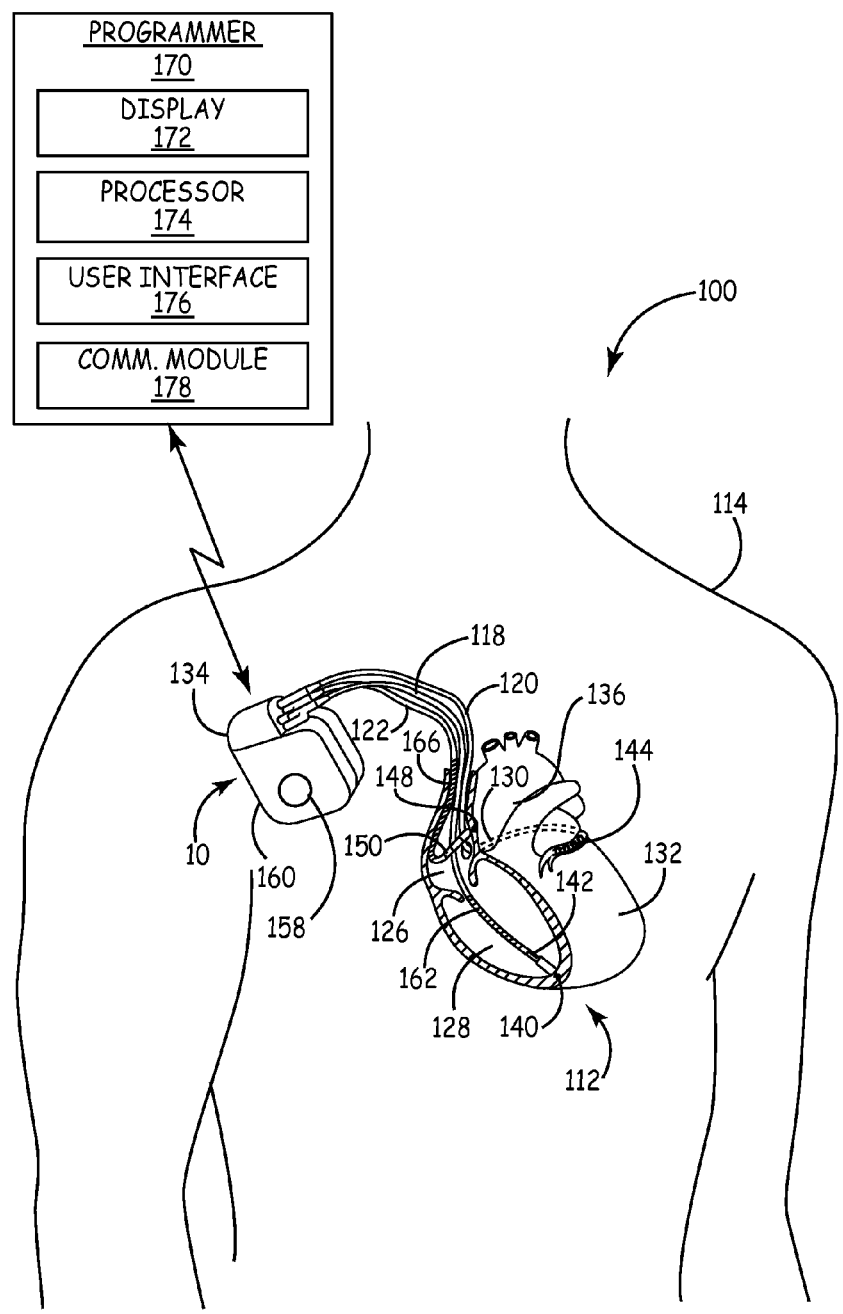
FIG. 1 is a schematic diagram of one embodiment of an implantable medical device (IMD) system in which techniques disclosed herein may be implemented to provide therapy to a patient's heart.

FIG. 1 is a schematic diagram of one embodiment of an IMD system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker, cardioverter, and/or defibrillator that provides electrical signals to heart 112 via electrodes coupled to one or more of leads 118, 120, and 122. IMD 10 is capable of delivering at least single chamber ventricular pacing in the left ventricle, and, in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac EGM signals using RV tip electrode 140 and RV ring electrode 142. RV lead 118 is shown to carry a coil electrode 162 which may be used for delivering high voltage cardioversion or defibrillation shock pulses.

IMD 10 senses LV EGM signals and delivers LV pacing pulses using the electrodes 144 carried by multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect arrhythmias of heart 112, such as fibrillation of ventricles 128 and 132, and deliver defibrillation therapy to heart 112 in the form of electrical pulses. While IMD 10 is shown in a right pectoral implant position in FIG. 1, a more typical implant position, particular when IMD 10 is embodied as an ICD, is a left pectoral implant position.

IMD 10 includes internal circuitry for performing the functions attributed to IMD 10, and a housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT therapy, which includes the use of a selected pacing vector for LV pacing that utilizes at least one electrode 144 on multipolar lead 120. IMD 10 is configured to pace in one or both ventricles 128 and 132 for controlling and improving ventricular synchrony. The methods described herein may be implemented in a single, dual or multi-chamber pacemaker or ICD delivering pacing pulses to at least the left ventricle using programmable pacing pulse timing parameters and programmable pacing vectors.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological or diagnostic information from IMD 10. A user may also interact with programmer 170 to program IMD 10, e.g., select values for operating parameters of the IMD. A user interacting with programmer 170 may request IMD 10 to perform a pacing site optimization algorithm and transmit results to programmer 170 or request data stored by IMD 10 relating to pacing site analysis procedures performed automatically by IMD 10 on a periodic basis.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, MICS, or as described in U.S. Pat. No. 5,683,432 "Adaptive Performance-Optimizing Communication System for Communicating with an Implantable Medical Device" (Goedeke, et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote management of a patient using the techniques described herein. Remote patient management systems may be configured to utilize the presently disclosed techniques to enable a clinician to review cardiac signal data and authorize programming of IMD pace control parameters. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming.

Figure 2:
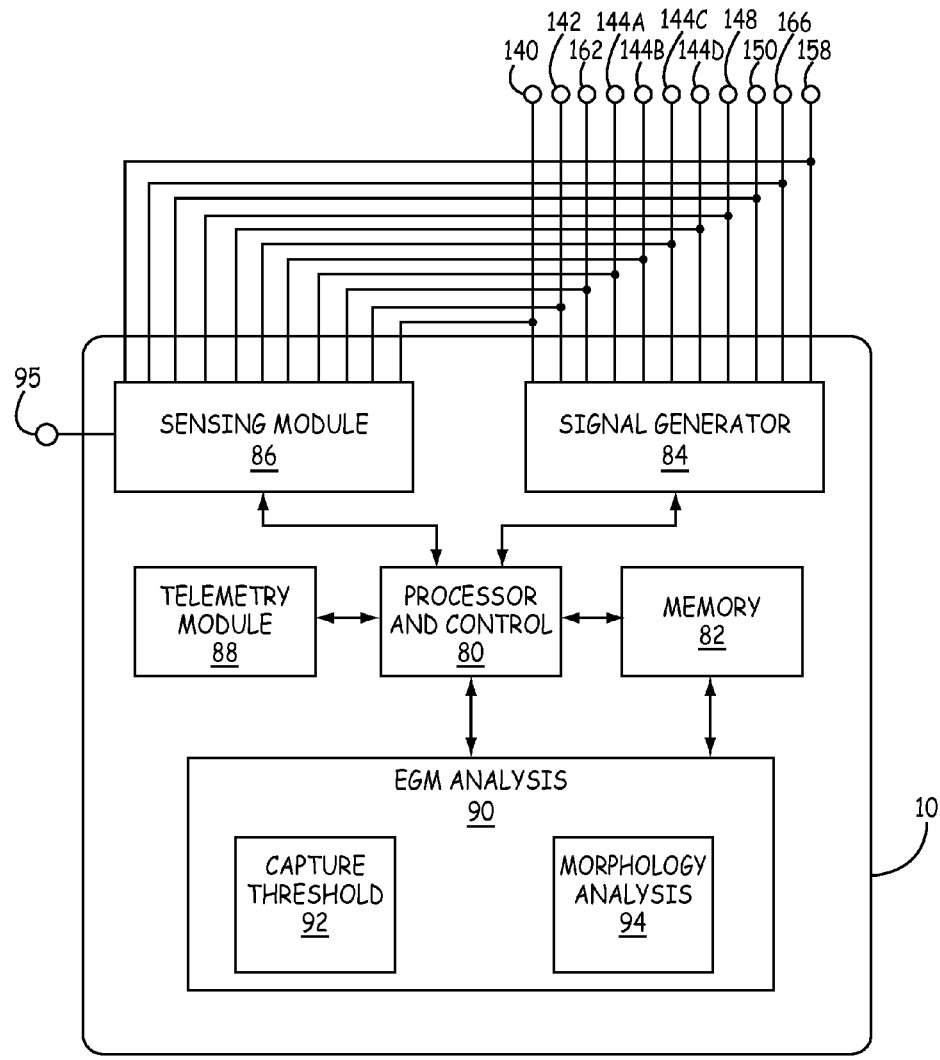
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, memory 82, signal generator 84, sensing module 86, and telemetry module 88. IMD 10 further includes EGM signal analysis module 90, which itself may include a capture threshold detection module 92 and an EGM morphology analysis module 94.

Memory 82 may include computer-readable instructions that, when executed by processor 80, cause IMD 10 and processor 80 to perform various functions attributed throughout this disclosure to IMD 10, processor 80, sensing module 86, and EGM analysis module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, EGM analysis module 90 may, at least in part, be stored or encoded as instructions in memory 82 that are executed by processor and control 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Processor and control 80 controls signal generator 84 to deliver cardiac pacing pulses according to atrial-ventricular (AV) and/or inter-ventricular (VV) timing intervals.

Signal generator 84 may include a switch module (not shown) and processor and control 80 may use the switch module to select, e.g., via a data/address bus, which of the available electrodes are used to deliver pacing pulses. Processor 80 may also control which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes. As will be described further below, processor and control 80 controls the switch module to select different LV electrodes 144 for delivering pacing pulses and measuring associated RV activation times in response to pacing at the different sites corresponding to electrodes 144. Selection of an LV pacing site during delivery of a pacing therapy is based on the measured RV activation times.

Sensing module 86 monitors cardiac signals from electrodes 140, 142, 144A-144D, 148, 150, 158, 162, or 166 in order to monitor electrical activity of heart 12. Sensing module 86 may also include a switch module to select which of the available electrodes are used to sense the cardiac activity. In some examples, processor 80 selects the electrodes to function as sense electrodes, or the sensing vector, via the switch module within sensing module 86.

Sensing module 86 includes multiple detection channels, each of which may be selectively coupled to respective combinations of electrodes 140, 142, 144A-144D, 148, 150, 158, 162, or 166 to detect electrical activity of a particular chamber of heart 112. Each detection channel may comprise an amplifier that outputs an indication to processor 80 in response to sensing of a cardiac depolarization, in the respective chamber of heart 112. In this manner, processor 80 may detect the occurrence of R-waves and P-waves in the various chambers of heart 12. The occurrence of R-waves sensed using a local bipolar sensing electrode pair is used in measuring relative activation times with respect to different candidate pacing sites for use in selecting a pacing site. Sensing of R-waves or other features of a QRS signal attendant to the depolarization of the myocardial tissue along a sensing electrode site in the RV is used to identify an LV pacing site associated with a relatively late activation of the RV.

In some embodiments, a far-field EGM signal is obtained by sensing module 86 for measuring the relative timing within the far-field QRS complex of a locally sensed R-wave in the RV (sensed using a local bipole) in response to pacing pulses delivered in the LV using electrodes 144. A potential LV pacing site is identified as one associated with a resultant RV R-wave that occurs relatively later in the far-field QRS complex as compared to other LV pacing sites. Sensing module 86 may provide an R-wave sense signal to EGM analysis module 90 indicating the time of sensed R-wave. EGM processing module 90 receives the R-wave sense signal and a far-field EGM signal. The EGM processing module 90 determines the onset and end of a far-field QRS complex and the timing of the R-wave sense signal relative to the far-field QRS complex.

Sensing module 86 may further include digital signal processing circuitry for providing EGM analysis module 90 with digitized EGM signals. Alternatively, analog EGM signals may be provided to EGM analysis module 90 and digitized as needed for performing EGM signal analysis.

EGM analysis module 90 may perform EGM signal analysis for use in selecting an LV pacing site. For example, a capture threshold module 92 may be included to detect capture and/or LOC when signal generator 84 delivers a pacing pulse. Capture threshold information may be used with other EGM analysis information for selecting pacing sites. EGM morphology analysis module 94 may be used for detecting fiducial points of near field EGM signals obtained from the RV sensing electrodes for measuring RV activation times relative to LV pacing pulses and/or relative to far field EGM QRS signals for identifying LV pacing sites associated with late activation at an RV sensing electrode site.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event, e.g., in another chamber.

It is further contemplated that methods described herein may be implemented using other physiological signals for determining optimal pacing parameters for delivering CRT. In some embodiments, another type of physiological sensor 95 other than cardiac electrodes is coupled to sensing module 86 and used for obtaining a signal correlated to the hemodynamic or mechanical function of the heart. Sensor 95 may be embodied as a mechanical, optical or other type of transducer, such as a pressure sensor, oxygen sensor, accelerometer, or any other sensor that is responsive to cardiac function and produces a signal corresponding to cardiac mechanical function. Analysis of the signal may be used in guiding selection of LV pacing site, AV and VV intervals used to control CRT pacing pulses.

Figure 3:
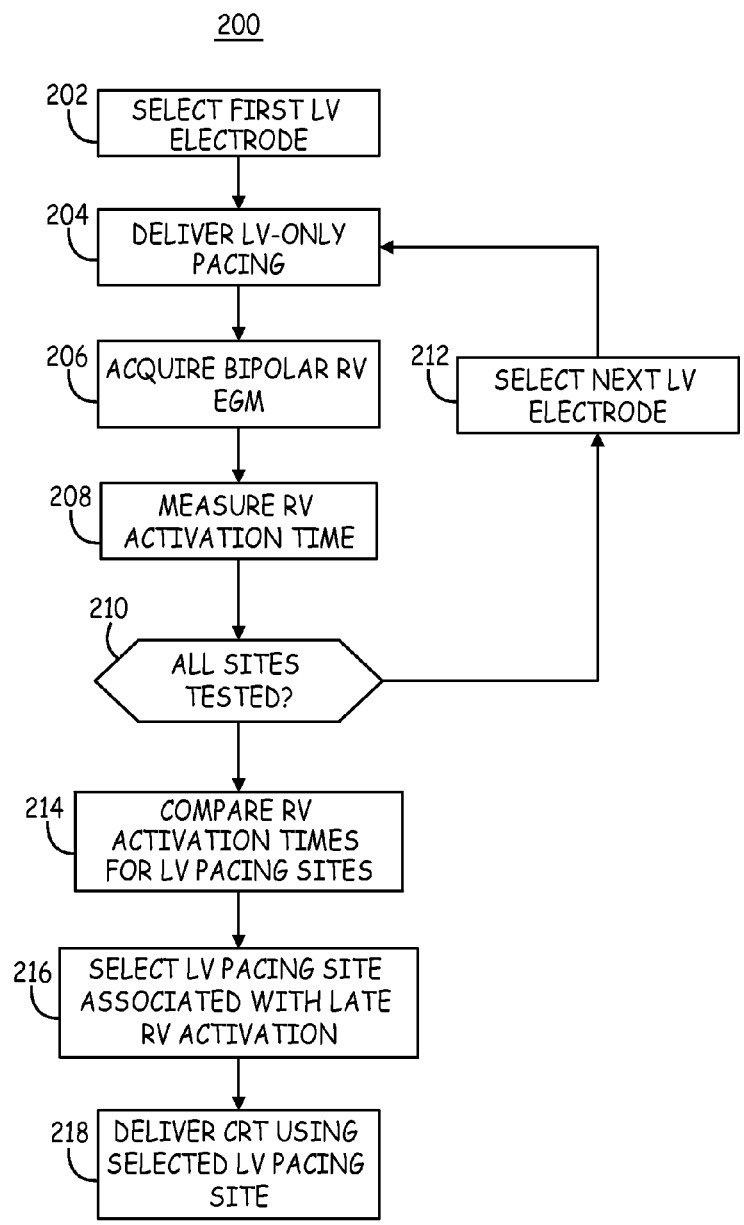
FIG. 3 is a flow chart of a method for controlling pacing electrode selection during a cardiac pacing therapy according to one embodiment.

FIG. 3 is a flow chart 200 of a method for controlling pacing electrode selection during a cardiac pacing therapy according to one embodiment. Flow chart 200 and other flow charts presented herein are intended to illustrate the functional operation of the device, and should not be construed as reflective of a specific form of software or hardware necessary to practice the methods described. It is believed that the particular form of software, firmware, hardware or combination thereof will be determined primarily by the particular system architecture employed in the device and by the particular signal sensing and therapy delivery methodologies employed by the device. Providing software, firmware, and/or hardware to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, an LV electrode is selected as a cathode to be tested as a possible LV pacing site. The candidate LV electrode is paired with an anode, which may be another LV electrode in a bipolar pacing vector or an electrode positioned away from the LV in a unipolar vector. If the LV electrode is tested in a bipolar combination with another LV electrode, steps may be taken to verify that anodal capture is not occurring in the LV when pacing using the cathode. Methods for detecting anodal capture are generally described in U.S. Pat. No. 8,626,291, hereby incorporated herein by reference in its entirety.

Single ventricle, LV-only pacing pulses are delivered at block 204. No pacing pulses are delivered in the RV. The atrial chambers may or may not be paced during LV-only pacing. LV-only pacing pulses are delivered shortly after the atrial excitation or at a rate higher than intrinsic sinus rate in order to achieve paced activation of the ventricles and avoid activation of the RV by intrinsic conduction from the atria. The timing of LV-only pacing pulses is controlled to promote a high likelihood that a sensed RV R-wave is a conducted depolarization arising from the LV pacing pulse. During atrial tracking modes of pacing, e.g. in a DDD/DDDR mode, the intrinsic AV conduction time may be measured for one or more cardiac cycles so that the LV-only pacing pulses can be delivered at an interval shorter than the intrinsic AV conduction time. During non-tracking pacing modes (e.g., VVI, VVIR, DDI, or DDIR), one or more intrinsic RR intervals may be measured such that the LV-only pacing pulses can be delivered earlier than a next anticipated intrinsic R-wave.

LV pacing pulses are delivered using the candidate LV electrode at a pacing pulse output that is above a capture threshold. Accordingly, selecting the candidate electrode and initiating LV-only pacing using the candidate electrode may include a determination of a capture threshold for the candidate electrode such that pacing pulses may be used at a predefined safety margin above the capture threshold. LV pace to RV sense conduction times can be influenced by the pacing voltage; a high voltage can shorten the conduction time. As such, to obtain meaningful comparisons between measurements obtained during pacing at different LV candidate electrodes, a standardized pacing pulse output based on capture thresholds may be used.

At block 206, an RV EGM signal is acquired using a bipolar RV sensing electrode pair, e.g. the RV tip and RV ring electrodes 140 and 142. A bipolar RV sensing pair is used to sense R-waves attendant to the local RV depolarizations. The IMD sensing module may provide processor and control 80 and/or EGM analysis module 90 R-wave sense signals or an EGM signal that may be digitized and analyzed to identify a fiducial point of a sensed QRS signal. The sensed R-waves or QRS fiducial points obtained from the RV EGM signal correspond to depolarizations conducted from the LV in response to the LV pacing pulse and are used to measure an RV activation time at block 208.

The RV activation time is the relative time from a reference point until the sensed R-wave or QRS fiducial point in the RV EGM. A sensed R-wave signal may be generated by a sense amplifier having an auto-adjusting sensing threshold. The reference point may be the LV pacing pulse but may be another reference point such as a P-wave, atrial pacing pulse, or LV evoked response.

After measuring the RV activation time corresponding to pacing at the currently selected candidate LV pacing electrode, if additional LV electrodes are available as determined at block 210, another LV electrode is selected as a candidate pacing electrode at block 212. The process of delivering LV-only pacing (block 204) and measuring a corresponding RV activation time (block 208) is repeated until RV activation times are measured for each candidate pacing electrode. RV activation time is measured while pacing at each candidate pacing site one at a time as opposed to simultaneous pacing at more than one LV pacing site such that an RV activation time can be measured for each LV pacing site individually. For example, in the embodiment shown in FIG. 1, LV pacing pulses may be delivered for one or more cardiac cycles using each of electrodes 144A-144D one at a time (as a cathode electrode paired with any available anode) and corresponding RV conduction times for each of the pacing sites corresponding to electrodes 144A-144D are measured. For accurate comparison of the LV pace to RV sense conduction times between different pacing sites, the cathodes may all be paired with the same anode during LV pace to RV sense conduction time measurements.

After RV activation times have been measured for all candidate LV pacing sites (electrode locations), the RV activation times are compared at block 214. An LV pacing site resulting in a relatively late RV activation time is selected as an LV pacing site for therapy delivery at block 216. A late activation time is an activation time that occurs relatively later than the RV activation time measured for another of the tested candidate LV pacing sites. The selected LV pacing site may correspond to a latest activation time measured, however, in some cases the latest activation time may correspond to an LV pacing site along myocardial scar tissue or locally ischemic tissue. As such, the selected LV pacing site is not necessarily the LV pacing site resulting in the latest RV activation time. As will be further described below, additional operations may be performed for rejecting LV pacing sites that are suspected of being along myocardial scar, locally ischemic tissue, or otherwise pathologically impaired tissue rendering the site undesirable as an LV pacing site for CRT.

In CRT, the greatest therapeutic benefit may be achieved when the LV is paced at or near a location associated with late intrinsic activation time of the left ventricle. In the methods disclosed herein, late activation time of the RV associated with pacing at a particular LV pacing site is expected to be indicative of an LV pacing site that will yield improvement in ventricular synchrony during CRT delivery. To determine an electrode site expected to improve ventricular synchrony, RV activation times are measured in response to LV pacing at different candidate pacing sites.

Selecting the LV pacing site at block 216 in response to the measured RV activation times may include automatic programming of the IMD to couple the LV pacing site electrode to the signal generator for pacing pulse delivery. Alternatively, selecting the LV pacing site may include transmitting the RV activation time data and/or a recommended LV pacing site based on the RV activation time data to programmer 170. A clinician may then select the recommended site and interacting with programmer 170 program the IMD to deliver LV pacing pulses using the selected LV pacing site.

At block 218, CRT is delivered using the selected LV pacing site electrode. Ventricular pacing may be LV-only pacing or biventricular pacing using at least the LV electrode at the selected site for delivering pacing in the LV. Single site, dual site or multi-site pacing may be delivered in the LV using the selected pacing site as at least one of the LV pacing sites. A second LV pacing site may be selected as the pacing electrode resulting in a next latest RV activation time. In one example, a second LV pacing site is selected as the LV site associated with a late electrical activation when the LV-only or biventricular pacing is performed using the first selected LV pacing site. Additional LV pacing sites may alternatively be selected as default pacing sites or based on additional hemodynamic, mechanical, or EGM assessments.

In one embodiment, after selecting the first LV pacing site using the method shown by flow chart 200, LV-only or biventricular pacing may be delivered using the selected LV pacing site electrode. LV activation times are measured at each of the remaining LV electrode sites during pacing at the first LV pacing site to identify a second LV pacing site corresponding to a late electrical activation compared to other candidate second LV pacing sites.

The LV pacing pulses delivered using the selected LV pacing site are delivered at a scheduled AV or VV interval, depending on whether LV-only pacing or biventricular pacing, respectively, is being delivered. The AV and VV intervals programmed for controlling the timing of the LV pacing pulses may be selected by a clinician based on clinical measurements, such as Doppler echocardiography, or selected automatically by the IMD based on EGM or other cardiac signal analysis. In one embodiment, an AV interval for LV-only pacing is selected as a percentage of a measured intrinsic atrial-ventricular conduction time. A VV interval for controlling timing of the LV pacing pulse during biventricular pacing may be selected based on a measured intrinsic AV conduction time, QRS signal width, measured RV activation time, or any combination thereof.

Figure 4:
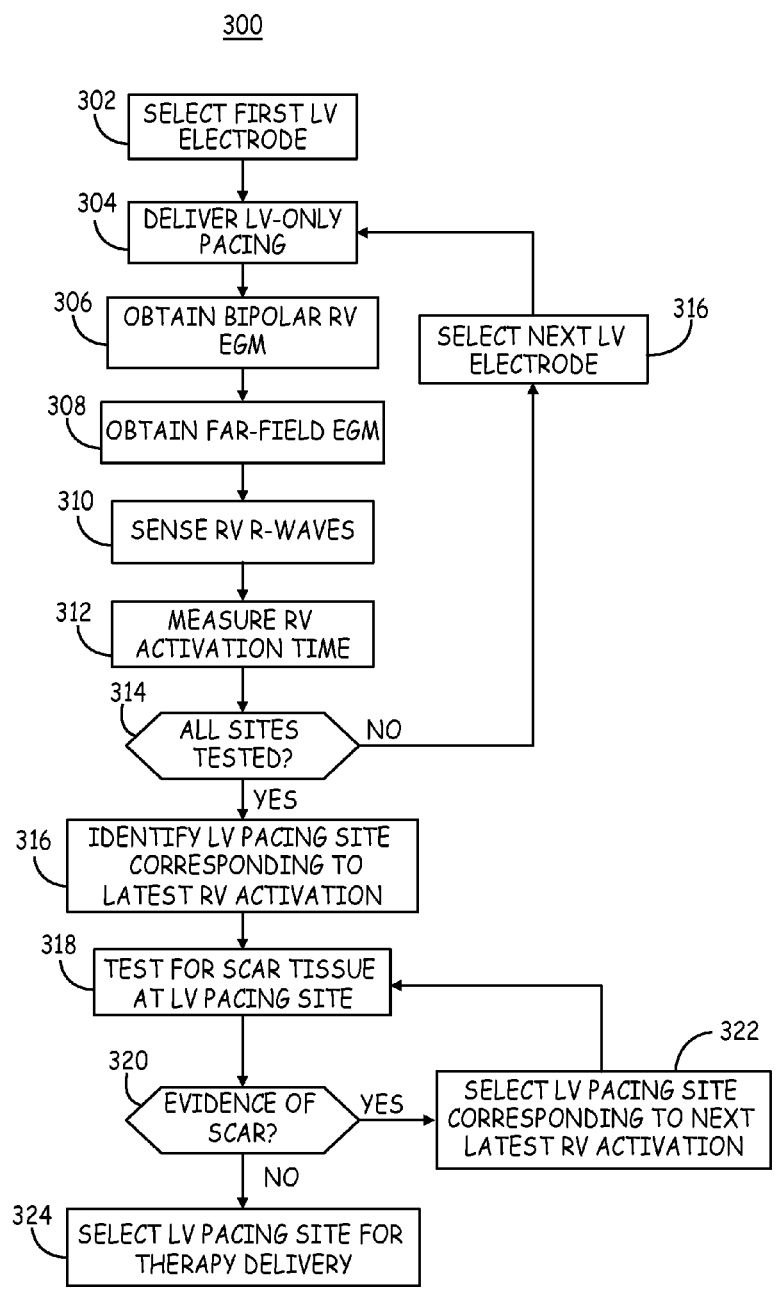
FIG. 4 is a flow chart of a method for controlling pacing electrode selection during a cardiac pacing therapy according to an alternative embodiment.

FIG. 4 is a flow chart 300 of a method for controlling pacing electrode selection during a cardiac pacing therapy according to an alternative embodiment. At block 302, a first candidate LV electrode is selected, and LV only pacing is delivered at block 304 using the candidate electrode paired with any available anode (that does not result in anodal capture of the LV). At block 306, a bipolar RV EGM signal is acquired for sensing R-waves (or fiducial points of the QRS signal) corresponding to a depolarization wavefront conducted to the RV myocardium in response to the LV-only pacing pulses.

At block 308, a far-field or unipolar EGM or ECG signal is obtained. The far-field or unipolar signal may be acquired using a coil electrode 162 and a housing electrode 158 in one example though other sensing vector combinations are possible for obtaining a relatively global signal representing depolarization of the right and left ventricular chambers. The far-field signal may be obtained using a sensing electrode positioned along the RV or LV paired with one or more sensing electrodes to obtain a sensing vector encompassing a substantially larger mass of the ventricular myocardium than a local bipolar sensing vector.

At block 310, RV R-waves (or QRS fiducial points) are sensed from the bipolar RV EGM signal. At block 312, the RV activation time is measured between the RV sensed R-wave or locally sensed QRS fiducial point and a reference point identified from the relatively more global QRS signal acquired from the far-field cardiac signal. This RV activation time is measured to determine how late the RV activation occurs in the relatively more global QRS signal complex.

If additional candidate LV electrodes are available, as determined at block 314, the next LV electrode is selected at block 316 and the process of delivering LV-only pacing using the next candidate electrode as a cathode paired with any available anode, which may be the same anode for all candidate cathodes, and measuring the RV activation time relative to a far-field QRS signal is repeated (blocks 304 through 312).

Once all candidate pacing electrodes have been tested (affirmative result at block 314), an LV pacing site corresponding to the latest RV activation time, i.e. the RV R-wave or QRS fiducial point occurring latest relative to the global far-field QRS signal complex, is identified at block 316. This LV pacing site corresponding to the latest RV activation is tested at block 318 for possible scar tissue, local ischemia, or other pathological condition that renders the site undesirable as a pacing site for CRT.

Testing for evidence of scar tissue or ischemia could include measuring the pacing capture threshold at the identified site. A high capture threshold, for example greater than a predefined threshold limit or determined to be significantly higher than the capture threshold at other pacing sites, may indicate a necrotic or ischemic tissue site. Alternatively or additionally, a test of evidence of scar tissue may include determining a time delay between pacing pulse delivery and initiation of an evoked response at or near the paced site or a fiducial point of a QRS complex acquired from a far-field EGM or ECG signal. Observation of delayed exit of a pacing-induced evoked response from that site (i.e., delayed initiation of QRS complex from the pacing pulse) is evidence of an undesirable pacing site for CRT.

In other embodiments, the QRS complex at the identified pacing site is sensed using the electrode at that site and analyzed to detect a relatively small amplitude or fractionated QRS signal. A small QRS complex or fractionated QRS complex in the EGM obtained using a short sensing bipole including the candidate pacing site electrode is evidence of myocardial scar tissue. A small or fractionated QRS complex would be identified from the EGM signal obtained using the electrode at the pacing site when pacing is not delivered at that site, i.e., either during intrinsic rhythm or possibly during pacing at a distant ventricular site.

If evidence of myocardial scar tissue, local ischemia or other pathological state of the tissue is detected based on a high capture threshold at the candidate site, delayed initiation of an evoked QRS complex in response to pacing at the candidate site, or small amplitude or fractionated locally sensed QRS complex during no pacing at the site, the site is rejected as an LV pacing site for delivering CRT. The LV pacing site corresponding to the next latest RV activation time is selected at block 322. This site may also be evaluated for any pathological abnormalities at blocks 318 and 320.

This process shown at blocks 318 through 322 is repeated until an LV pacing site is identified that corresponds to a late RV activation time and does not present evidence of scar. The identified pacing site is selected at block 324 for LV pacing during CRT delivery. Site selection may include automatic programming of the LV pacing vector(s) using the selected site as a cathode and/or transmitting the recommended site and RV activation time data to programmer 170 to enable a clinician to review the data and manually program a selected LV pacing site.

It is unlikely that all possible pacing sites will be evaluated without identifying a late activation site that does not present evidence of scar, but if that situation does arise a recommendation to reposition the LV pacing lead may be made. Additionally or alternatively, an LV pacing site having the lowest capture threshold, shortest exit time to the evoked QRS complex, and/or most "normal" sensed QRS morphology (e.g., least diminished QRS amplitude or non-fractionated QRS signal complex) may be selected as the best possible LV pacing site at block 324.

It is also recognized that there could be other reasons for rejecting a latest activation site, such as a high capture threshold, out of range impedance, presence of anodal or extra-cardiac stimulation, or other lead/electrode acceptance or rejection criteria.

Figure 5:
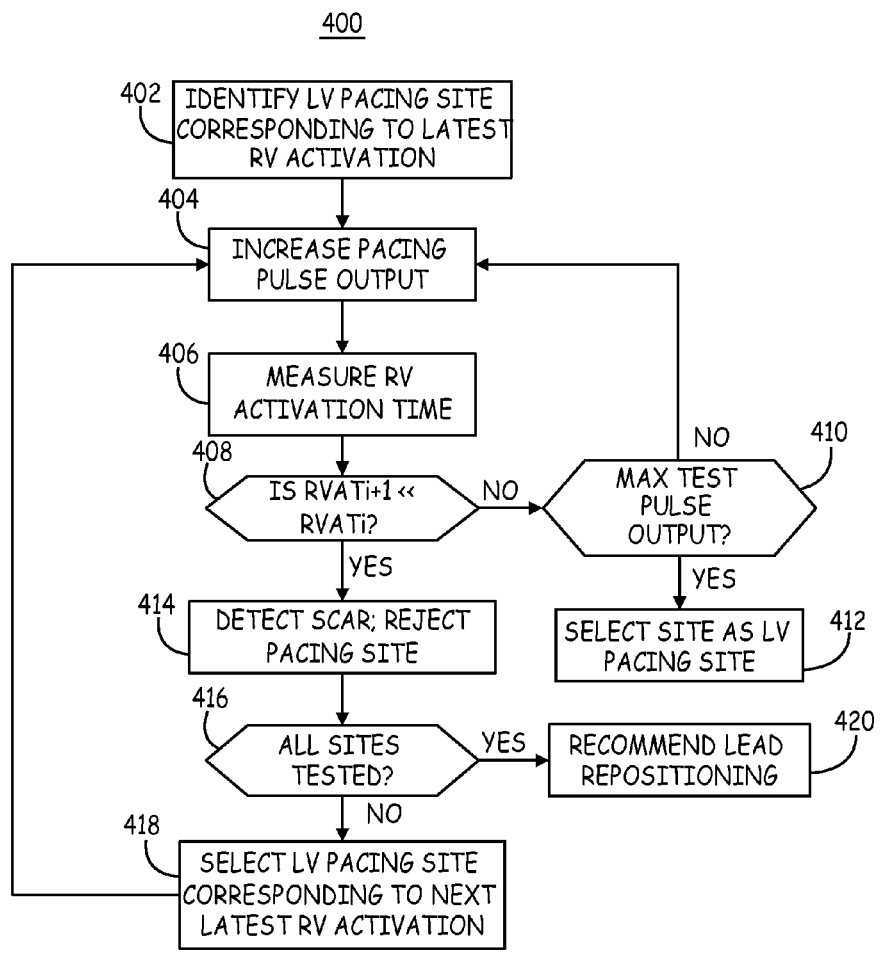
FIG. 5 is a flow chart of a method for controlling LV pacing site selection for a cardiac pacing therapy according to yet another embodiment.

FIG. 5 is a flow chart 400 of a method for controlling LV pacing site selection for a cardiac pacing therapy according to yet another embodiment. At block 402, an LV pacing site corresponding to the latest RV activation time is identified using the methods described above in conjunction with FIG. 3 or 4. At block 404, LV pacing pulses are delivered to the identified pacing site at a pacing pulse output that is increased relative to the pacing pulse output used to identify the LV pacing site as a site corresponding to the latest RV activation. The pacing pulse output may be increased by increasing the pulse amplitude or the pulse width.

Measurement of RV activation time is repeated at block 406 during pacing at the increased pacing pulse output. This new RV activation time, $RVAT_{i+1}$ is compared to the originally measured, latest RV activation time at block 408. If the new RV activation time is significantly less than the originally measured RV activation time ($RVAT_i$), myocardial scar tissue or otherwise pathologically impaired tissue is detected at block 414. The identified site is rejected as an LV pacing site for therapy delivery.

While a gradual and small decrease in RV activation time due to increased pacing pulse output is expected, a sudden relatively large decrease in RV activation time due to increased pacing pulse amplitude suggests that the myocardial tissue along the pacing electrode is scar tissue or otherwise impaired. A sudden decrease is detected as a change in RV activation time that is greater than a predefined threshold, which may be a percentage or portion of the originally measured latest RV activation time or other previously measured RV activation time, for a given increment in pacing output. As such, if there is a relatively large difference between RV activation times measured for two consecutive pacing pulse output levels, the pacing site is rejected. In some cases, a sudden change in the RV activation time may also be an electrode or lead related issue which would still render the LV electrode undesirable as a pacing electrode during CRT.

If a sudden decrease in RV activation time due to an incremental increase in pacing pulse output is detected, and if additional LV electrodes are available, as determined at block 416, another LV pacing site electrode corresponding to the next latest RV activation time (as originally measured using the methods of FIG. 3 or 4) is selected at block 418. The process returns to block 404 and repeats measurements of RV activation times at incrementally increasing pacing pulse output to determine if a sudden decrease in RV activation time occurs.

The pacing pulse output is increased, e.g. by stepwise increases in amplitude or in pulse width, until a maximum pacing pulse output is reached at block 410. A maximum output may be a maximum of a defined range for performing the test or a maximum available output from the IMD. If the maximum pacing pulse output is reached at block 410 without detecting a sudden drop in RV activation time for consecutive incrementally increased pacing pulse outputs, the LV pacing site is selected at block 412 for use during CRT delivery. The stepwise increases in pacing pulse output may be performed in conjunction with capture threshold tests.

Infrequently, the situation may arise that all available LV pacing site electrodes result in a sudden drop in RV activation time due to an increase in pacing pulse output. In this case, a warning to the clinician may be generated recommending that the LV lead be repositioned at block 420.

There is also a possibility that anodal capture occurs upon increasing the pacing pulse output and the sudden addition of anodal stimulation simultaneously with cathodal stimulation could abruptly change the RV activation time. As such, in some embodiments, EGM signal analysis may include detection of the presence of anodal capture. A sudden change in RV activation time due to the presence of anodal capture would not eliminate the pacing site as a possible therapy delivery site.

In the flow charts presented herein, it is contemplated that all blocks shown may not be performed in some embodiments or may be performed in a different order than the order shown. Furthermore, operations described in conjunction with separate flow charts presented herein may be combined in any combination to successfully achieve the result of selecting a pacing site electrode along a heart chamber.

Thus, a medical device and associated methods for controlling and delivering a pacing therapy have been presented in the foregoing description with reference to specific embodiments. It is appreciated that various modifications to the referenced embodiments may be made without departing from the scope of the disclosure as set forth in the following claims.

The invention claimed is:

1. A method for controlling a cardiac therapy, the method comprising:
   delivering pacing pulses to a patient's left ventricle at a plurality of pacing sites one at a time;
   determining right ventricular activation times in response to the pacing pulses being delivered at each of the plurality of pacing sites; and
   selecting a left ventricular pacing site in response to the determined right ventricular activation times, wherein selecting the left ventricular pacing site comprises:
   identifying a left ventricular pacing site from the plurality of pacing sites with an associated first activation time that is the latest determined right ventricular activation time compared to the other right ventricular activation times associated with the other plurality of pacing site;
   increasing a pacing output delivered to the identified left ventricular pacing site;
   determining a second activation time of the right ventricle in response to the increased pacing output; and
   rejecting the identified left ventricular pacing site with the associated first activation time in response to the second activation time being less than the first activation time.

2. A method for controlling a cardiac therapy, the method comprising:
   delivering pacing pulses to a patient's left ventricle at a plurality of pacing sites one at a time;
   determining right ventricular activation times in response to the pacing pulses being delivered at each of the plurality of pacing sites;
   selecting a left ventricular pacing site in response to the determined right ventricular activation times;
   identifying a left ventricular pacing site from the plurality of pacing sites with an associated first activation time that is the latest determined right ventricular activation time compared to the other right ventricular activation times associated with the other plurality of pacing site;
   increasing a pacing output delivered to the identified site in multiple increments;
   determining an activation time of the right ventricle in response to each incrementally increased pacing outputs;
   determining activation time differences between the incrementally increased pacing outputs; and
   rejecting the pacing site as a left ventricular pacing site in response to an activation time difference between one pacing output and a next incrementally increased pacing output exceeding a threshold.

3. The method of claim 2, wherein the threshold is a portion of the latest activation time.

4. A method for controlling a cardiac therapy, the method comprising:
   delivering pacing pulses to a patient's left ventricle at a plurality of pacing sites one at a time;
   determining right ventricular activation times in response to the pacing pulses being delivered at each of the plurality of pacing sites;
   selecting a left ventricular pacing site in response to the determined right ventricular activation times;
   obtaining a far field cardiac electrical signal and a near field right ventricular electrogram signal; and
   determining the activation times in response to determining a time of an R-wave sensed from the near field right ventricular signal relative to a QRS signal sensed from the far field signal, wherein selecting the left ventricular pacing site comprises selecting one of the plurality of pacing sites associated with a sensed right ventricular R-wave occurring later relative to the QRS signal than a sensed right ventricular R-wave associated with another of the plurality of pacing sites.

5. A medical device for controlling and delivering a pacing therapy, the device comprising:
   a plurality of electrodes;
   a signal generator coupled to the plurality of electrodes to deliver cardiac pacing pulses;
   a sensing module coupled to the plurality of electrodes to sense cardiac signals; and
   a controller coupled to the signal generator and the sensing module and configured to:
   control the signal generator to deliver pacing pulses to a patient's left ventricle at a plurality of pacing sites one at a time;
   determine right ventricular activation times in response to the pacing pulses being delivered at each of the plurality of pacing sites; and
   select a left ventricular pacing site in response to the determined right ventricular activation times, wherein selecting the left ventricular pacing site comprises:
   identifying a left ventricular pacing site from the plurality of pacing sites with an associated first activation time that is the latest determined right ventricular activation time compared to the other right ventricular activation times associated with the other plurality of pacing site;
   increasing a pacing output delivered to the identified left ventricular pacing site;
   determining a second activation time of the right ventricle in response to the increased pacing output; and
   rejecting the identified left ventricular pacing site with the associated first activation time in response to the second activation time being less than the first activation time.

6. A medical device for controlling and delivering a pacing therapy, the device comprising:
   a plurality of electrodes;
   a signal generator coupled to the plurality of electrodes to deliver cardiac pacing pulses;
   a sensing module coupled to the plurality of electrodes to sense cardiac signals; and
   a controller coupled to the signal generator and the sensing module and configured to:
   control the signal generator to deliver pacing pulses to a patient's left ventricle at a plurality of pacing sites one at a time;
   determine right ventricular activation times in response to the pacing pulses being delivered at each of the plurality of pacing sites;

select a left ventricular pacing site in response to the determined right ventricular activation times;
identify a left ventricular pacing site from the plurality of pacing sites with an associated first activation time that is the latest determined right ventricular activation time compared to the other right ventricular activation times associated with the other plurality of pacing site;
increase a pacing output delivered to the identified site in multiple increments;
determine an activation time of the right ventricle in response to each incrementally increased pacing outputs;
determine activation time differences between the incrementally increased pacing outputs; and
reject the pacing site as a left ventricular pacing site in response to an activation time difference between one pacing output and a next incrementally increased pacing output exceeding a threshold.

7. The device of claim 6, wherein the threshold is a portion of the latest activation time.

8. A medical device for controlling and delivering a pacing therapy, the device comprising:
a plurality of electrodes;
a signal generator coupled to the plurality of electrodes to deliver cardiac pacing pulses;
a sensing module coupled to the plurality of electrodes to sense cardiac signals;
electrodes to obtain a far field cardiac electrical signal; and
a controller coupled to the signal generator and the sensing module and configured to:
control the signal generator to deliver pacing pulses to a patient's left ventricle at a plurality of pacing sites one at a time;
determine right ventricular activation times in response to the pacing pulses being delivered at each of the plurality of pacing sites; and
select a left ventricular pacing site in response to the determined right ventricular activation times;
obtain a near field right ventricular electrogram signal and a far-field QRS signal;
determine the activation times by determining a time of an R-wave sensed from the near field right ventricular signal relative to a QRS signal sensed from the far field signal; and
select the left ventricular pacing site comprising selecting one of the plurality of pacing sites associated with a sensed right ventricular R-wave occurring later relative to the QRS signal than a sensed right ventricular R-wave associated with another of the plurality of pacing sites.

9. A non-transitory computer-readable medium storing instructions which cause a medical device to perform a method for controlling a cardiac therapy, the method comprising:
delivering pacing pulses to a patient's left ventricle at a plurality of pacing sites one at a time;
determining right ventricular activation times in response to the pacing pulses being delivered at each of the plurality of pacing sites; and
selecting a left ventricular pacing site in response to the determined right ventricular activation times, wherein selecting the left ventricular pacing site comprises:
identifying a left ventricular pacing site from the plurality of pacing sites with an associated first activation time that is the latest determined right ventricular activation time compared to the other right ventricular activation times associated with the other plurality of pacing site;
increasing a pacing output delivered to the identified left ventricular pacing site;
determining a second activation time of the right ventricle in response to the increased pacing output; and
rejecting the identified left ventricular pacing site with the associated first activation time in response to the second activation time being less than the first activation time.

* * * * *